United States Patent [19]
Wegman

[11] Patent Number: 6,022,539
[45] Date of Patent: Feb. 8, 2000

[54] AMELIORATION OF PEYRONIE'S DISEASE

[75] Inventor: Thomas L. Wegman, North Merrick, N.Y.

[73] Assignee: Advance Biofactures of Curacao, Curacao, Netherlands Antilles

[21] Appl. No.: 09/325,224

[22] Filed: Jun. 3, 1999

[51] Int. Cl.[7] .................................................. A61K 38/48
[52] U.S. Cl. .......................................................... 424/94.67
[58] Field of Search ........................................... 424/94.67

[56] References Cited

U.S. PATENT DOCUMENTS 4,338,300  7/1982  Gelbard ................................ 424/94.67

OTHER PUBLICATIONS

M. K. Gelbard, et al. Collagenase for Peyronie's Disease . . . Urology Research (1982) 10: 135–140.
M. K. Gelbard, et al. The Use of Collagenase in the Treatment of Peyronie's Disease, J. of Urology, v. 134, p. 280–283 (Aug. 1985).
R. G. Hamilton et. al. Humoral Immune Response in Peyron Disease Patients Receiving . . . J. Urology (Mar. 1986) v. 135, pp. 641–647.
M. K. Gelbard, "Controlled Vacuum . . . Deformity" Urology (Oct. 1990) v. 36, #4. pp. 367–369.
F. Bernard, et. al. "Arterial Evaluation . . . " in J. Rajfer Common Problems in Infertility and Impotence, Chicago. Year Book Medical Publishers 1990 p 258–265.
M. K. Gelbard, et. al. Collagenase Versus . . . in Treatment of Peyro J Urology, (Jan. 1993) v. 149 pp. 56–58.

*Primary Examiner*—Jean C. Witz
*Attorney, Agent, or Firm*—John D. Upham; Roland Plottel

[57] ABSTRACT

A method of treating an individual suffering from Peyronie's disease. Collagenase is injected into a fibrous Peyronie's plaque in the penis of the individual suffering from the disease. The penis immediately after injection, is immobilized and maintained immobile for several hours. The collagenase is in a pharmaceutically acceptable carrier in a concentration of about 20,000 to about 40,000 ABC units per ml., and the amount and concentration of the collagenase is effective to soften and/or rupture the plaque whereby the erectile deviation caused by the plaque is ameliorated

16 Claims, No Drawings

AMELIORATION OF PEYRONIE'S DISEASE

Peyronie's disease is an idiopathic condition resulting in penile deformity and disability as the result of scarring and contracture within the tunica albugines of the corpora cavernosa. The scarring takes the form of plaques or masses of dense fibrous tissue.

BRIEF SUMMARY OF THE INVENTION

Collagenase is injected into the Peyronie's plaque, and the penis immobilized for several hours. Suitable dosages, concentration, and frequency of injections are described below.

BACKGROUND

Gelbard, M. K., Walsh, R., Kaufman, J. J. Collagenase for Peyronie's Disease Experimental Studies, Urol. Res. 10:135–140, 1982. This in vitro pilot study in which Peyronie's plaques were digested in collagenase solution, led to the estimate that the dose required for an effect on Peyronie's plaques in vivo is in the range of 100 to 400 units of Worthington collagenase as a 0.5% solution.

Gelbard, U.S. Pat. No. 4,338,300, issued Jul. 6, 1982, teaches treating Peyronie's disease by administering collagenase directly into the plaques. This patent repeats the data in Gelbard, Walsh and Kaufman, Urol. Res., 10:135–140, 1982 cited above.

Gelbard, M. K., Lindner, A., Kaufman, J. J. The Use of Collagenase in the Treatment of Peyronie's Disease, The Journal of Urology: 134:280–283, 1985. These authors report treatment of 31 men with a history of Peyronie's disease. A dose of 470 Advance Biofactures units [ABC units] per intralesional injection on 3 consecutive days was proposed. The first 6 patients received total doses ranging from 270 to 1,595 units (mean 803). The dose was increased gradually and the next 25 patients received 1,739 to 4,850 units total (mean 2,695). Concentrations of the collagenase were 470 to 620 units per cc in the first 15 patients and then 910 units per cc in the remainder. Of the 31 patients, 20 (65%) reported objective improvement. The authors speculated that the efficacy may be improved by repeated doses, possibly at higher levels Hamilton, R. G., Mintz, G. R., Gelbard, M. K., Humoral Immune Responses in Peyronie's Disease Patients Receiving Clostridial Collagenase Therapy, The Journal of Urology: 135:641–647, 1986. This study determined human IgG and IgE antibody responses to clostridial collagenase in untreated healthy blood donors and in patients receiving intrapenile injections of collagenase for treatment of Peyronie's disease. Injections were of 3,000 to 12,650 ABC units purified collagenase. Clinical results of effects on the disease were not reported.

Gelbard, M. K., James, K., Riach, P., Dorel, F., Collagenase Versus Placebo in the Treatment of Peyronie's Disease: A Double-Blind Study, The Journal of Urology, 149:56–58, January 1993. Peyronie's disease patients were grouped into 3 categories. Category 1 had a penile bend of 30 degrees or less and/or palpable plaque less than 2 cm. in extent; category 2 displayed 30 to 60 degrees and/or 2 to 4 cm.; category 3 had greater than 60 degrees of angular deviation and/or greater than 4 cm. of palpable plaque. Purified collagenase in the amount of 2,000 advance biofactor units [ABC units] in 0.5 cc of diluent was administered intralesionally in total amounts of 6,000 units to category 1 patients, 10,000 units to category 2, and 14,000 units to category 3. Overall, positive responses were noted in 36% of the treatment group versus 4% in the placebo group. The maximum angular improvement ranged from 15 to 20 degrees. Only 1 positive response out of 8 treated category 3 patients was noted; this was not statistically significant.

DETAILED DESCRIPTION

Collagenase is an enzyme that has the specific ability to digest collagen. It is derived commercially from fermentation by *Clostridium histolyticum*, and is purified by a chromatographic technique. It is available in several levels of purity, containing from substantial to essentially zero amounts of other proteinases.

The potency assay of collagenase is based on the digestion of undenatured collagen (from bovine tendon) at pH 7.2 and 37 degrees C. for 20–24 hours. The number of peptide bonds cleaved are measured by reaction with ninhydrin. Amino groups released by a trypsin digestion control are subtracted. One net ABC unit of collagenase will solubilize ninhydrin reactive material equivalent to 1.09 nanomoles of leucine per minute.

Sterilized lyophilized collagenase powder is available having a minimum assay of 50 ABC units per mg. The assay may range considerably above that from batch to batch, but is taken into account in determining the weight of powder to use with a pharmaceutically acceptable carrier, e.g. normal saline, in preparing a desired concentration for treatment.

The collagenase is applied in a liquid carrier that is pharmaceutically acceptable, including inertness towards the collagenase. Examples are normal saline, aqueous NaCl/CaCl2 buffer, aqueous dextran solution, aqueous hetastarch solution. Aqueous carriers are preferred.

In accordance with an aspect of the invention, collagenase in a liquid carrier is injected into a fibrous Peyronie's plaque and immediately thereafter the penis is immobilized, as by wrapping with sufficient gauze bandage and in such a way as to form a bulky dressing, and/or by the patient's donning an athletic supporter. The penis is thus prevented from substantial movement. The immobilization is continued for several hours, e.g. 4 to 12 hours. Typically, if the injection takes place during the early part of the afternoon, the dressing/support is removed at bedtime. This procedure results in good clinical outcomes.

The amount and concentration of collagenase used are effective to soften and/or rupture the plaque. The deformity caused by the plaque that has been holding the penis bent being thus relieved, the penis soon straightens to a considerable extent, often completely.

It is preferred to inject sufficient collagenase solution into the Peyronie's plaque to provide a total amount of at least about 20,000 ABC units of collagenase in a pharmaceutically acceptable carrier in a concentration of about 20,000 to about 40,000 ABC units per ml. The total amount may be applied by way of one or more injections. The maximum cumulative total dosage is usually limited to about 60,000 ABC units.

In an important aspect of the invention, the effects of Peyronie's disease are ameliorated by injecting into a Peyronie's plaque a series of at least two injections of at least about 10,000 ABC units each of collagenase at least one day apart to provide a total amount of at least about 20,000 ABC units. Preferably each injection is of about 10,000 to about 20,000 ABC units, in a concentration of about 20,000 to about 40,000 ABC units per ml. At the present time it is deemed advisable that the maximum cumulative total dosage should not exceed about 60,000 ABC units.

For example, a suitable series may constitute at least three injections during a period of not over ten days. Another suitable series is approximately weekly injections of about 10,000 to about 20,000 ABC units each. A series should not exceed a maximum cumulative total dosage of about 60,000 ABC units. High concentrations of about 20,000 to about 40,000 ABC units per ml are desirable. In general, the lower the amount of collagenase, the greater should be the concentration.

In cases where results of a single series of treatments are considered inadequate after 3 months, a second series may be given, ordinarily with the total amount of collagenase and concentration within the ranges heretofore given, and with a second maximum of 60,000 units.

EXPERIMENTAL

In all of the experimental work, Nucleolysin® from Advance Biofactures Corporation of Lynbrook, N.Y., was used. This is collagenase obtained by fermentation of *Clostridium histolyticum*, purified by chromatography, and lyophilized. It is substantially free from other proteinases. It was diluted to desired concentration with an aqueous buffer of 0.2 mM calcium chloride and 0.9% sodium chloride.

The collagenase solution is distributed throughout the length of the lesion by inserting the needle into the lesion and injecting as the needle is withdrawn. If the plaque is irregular, the needle is redirected to the sides in a fan-like fashion while injecting into those areas as well, in order to distribute the dose uniformly within the lesion. The injections are made directly into the plaque in a flaccid penis or at the point of maximum concavity under an artificial erection. A small amount of anaesthetic, e.g. lidocaine, may be used if necessary.

Following the injection, the penis was immobilized as described earlier.

A patient was presented with penile curvature due to Peyronie's disease of 65°, as measured by controlled vacuum chamber for standardized photographic documentation of erectile deformity. The patient was injected three times within a one week period with 10,000 ABC units in 0.25cc buffer for each injection. Injections took place on Tuesday, Thursday, and Friday. Following the second injection, the plaque was observed to be considerably softer and more compliant. Post each injection, the patient wore an athletic supporter for 12 hours to immobilize the penis and avoid any extravasation of the collagenase. The physician was able to physically rupture the plaque with manipulation.

The patient is very pleased with the treatment results. The patient underwent vacuum chamber studies at 3 months post injection and the photographs indicate a 60% decrease in penile curvature.

Twenty-two patients have been treated under this regimen and all but one have been satisfied.

I claim:

1. A method of treating an individual suffering from Peyronie's disease which comprises injecting collagenase into a fibrous Peyronie's plaque in the penis of the individual suffering from the disease, immobilizing the penis immediately after injection, and maintaining the penis immobile for several hours, the collagenase being in a pharmaceutically acceptable carrier in a concentration of about 20,000 to about 40,000 ABC units per ml., and the amount and concentration of the collagenase being effective to soften and/or rupture the plaque whereby the erectile deviation caused by the plaque is ameliorated.

2. A method according to claim 1 wherein a total amount of at least about 20,000 ABC units of collagenase are applied in one or more injections.

3. A method according to claim 1 wherein the maximum cumulative total dosage does not exceed about 60,000 ABC units.

4. A method according to claim 1 wherein the period of immobility is from about 4 to about 12 hours.

5. A method according to claim 1 wherein that method is repeated after about 3 months.

6. A method according to claim 1 wherein the collagenase is in an aqueous carrier.

7. A method of treating an individual suffering from Peyronie's disease which comprises injecting into a fibrous Peyronie's plaque in the penis of the individual suffering from the disease a series of at least two injections of at least about 10,000 ABC units each of collagenase at least one day apart to provide a total amount of at least about 20,000 ABC units, the amount and concentration of the collagenase being effective to soften and/or rupture the plaque whereby the penile flexure caused by the plaque is ameliorated.

8. A method according to claim 7 wherein each injection is of about 10,000 to about 20,000 ABC units.

9. A method according to claim 7 wherein the collagenase is supplied in a pharmaceutically acceptable carrier in a concentration of about 20,000 to about 40,000 ABC units per ml.

10. A method according to claim 7 wherein the maximum cumulative dosage does not exceed about 60,000 ABC units.

11. A method according to claim 7 wherein a series of at least 3 injections is made during a period of not over ten days.

12. A method according to claim 7 wherein a series of approximately weekly injections of about 10,000 to about 20,000 ABC units each is made up to a maximum cumulative total dosage not to exceed about 60,000 ABC units.

13. A method according to claim 7 wherein another series of injections is made after 3 months.

14. A method according to claim 7 wherein the collagenase is in an aqueous carrier.

15. A method according to any one of claims 1–6 further comprising after the step of immobilization, then physically rupturing the plaque by manipulation.

16. A method according to any one of claims 7–14 further comprising the step of physically rupturing the plaque by manipulation.

* * * * *